United States Patent [19]

Shim

[11] 4,036,789

[45] July 19, 1977

[54] POLYURETHANE FOAMS PREPARED FROM MIXED POLYALKYLENE GLYCOL POLYPHOSPHOROUS COMPOUNDS

[75] Inventor: Kyung S. Shim, Irvington, N.Y.

[73] Assignee: Stauffer Chemical Company, Westport, Conn.

[21] Appl. No.: 525,239

[22] Filed: Nov. 19, 1974

Related U.S. Application Data

[60] Division of Ser. No. 389,608, Aug. 20, 1973, Pat. No. 3,878,270, which is a division of Ser. No. 166,289, July 26, 1971, Pat. No. 3,798,290, which is a continuation-in-part of Ser. No. 86,313, Nov. 2, 1970, Pat. No. 3,819,750, which is a continuation-in-part of Ser. No. 63,262, Aug. 6, 1970, abandoned.

[51] Int. Cl.$^2$ ............................................. C08G 18/14
[52] U.S. Cl. ........................... 260/2.5 AR; 260/2.5 AJ
[58] Field of Search .................... 260/2.5 AJ, 2.5 AR

[56] References Cited

U.S. PATENT DOCUMENTS

| 3,027,349 | 3/1962 | Bahr et al. | 260/2.5 AJ |
|---|---|---|---|
| 3,159,605 | 12/1964 | Friedman | 260/953 |
| 3,850,859 | 11/1974 | Wortmann | 260/2.5 AJ |

FOREIGN PATENT DOCUMENTS

| 658,416 | 2/1963 | Canada | 260/2.5 AJ |
|---|---|---|---|

*Primary Examiner*—Eugene C. Rzucidlo
*Attorney, Agent, or Firm*—William R. Robinson

[57] ABSTRACT

Mixed polyalkylene glycol polyphosphorus compounds containing both phosphite and vinyl phosphate linkages are prepared by reacting certain polyalkylene glycol polyphosphites with less than a stoichiometric amount of a halogenated carbonyl compound.

2 Claims, No Drawings

POLYURETHANE FOAMS PREPARED FROM MIXED POLYALKYLENE GLYCOL POLYPHOSPHOROUS COMPOUNDS

RELATED APPLICATION

This is a division of application Ser. No. 389,608 filed Aug. 20, 1973, now U.S. Pat. No. 3,878,270, which in turn is a division of application Ser. No. 166,289, filed July 26, 1971, now U.S. Pat. No. 3,798,290.

This application is a continuation-in-part of Application Ser. No. 86,313 filed Nov. 2, 1970, now U.S. Pat. No. 3,819,750 which in turn is a continuation in part of Application Ser. No. 63,262 filed Aug. 6, 1970, now abandoned by Kyung Sup Shim.

BACKGROUND OF THE DISCLOSURE

In the polyurethane field, increased interest is being shown in compounds which can be added to the polyurethane polymers to act as fire retardant agents. Particular interest is being shown in compounds which have functional groups reactive with the polyol or polyisocyanate used in preparing the polyurethane so that the fire retardant agent can be copolymerized into the polymer chain. One such group of reactive flame retardants are the polyalkylene glycol phosphites such as those described in U.S. Pat. No. 3,009,939. However, these materials, due to their high OH numbers and crosslinking tendency, are unsuitable for use in flexible urethane foams. In U.S. Pat. Nos. 3,081,331 and 3,142,651, there is disclosed a method of forming polyalkylene glycol polyphosphites having up to 10 phosphite groups in the polymer chain by reacting a trialkyl phosphite with a polypropylene glycol in a molar ratio of 2.1 to 2.5 moles of glycol per mole of phosphite. These materials are also unsuitable for use in flexible urethane foams as a result of their high OH numbers and their tendency to crosslink.

Another attempt at employing reactive flame retardants, described in U.S. Pat. Nos. 3,142,651 and 3,092,651, involves the use of polypropylene glycol poly-hydrogenphosphonates produced by a thermal polymerization. Likewise, polyalkylene glycol hydrogen polyphosphonates have also been produced by transesterifying a secondary hydrogen phosphonate with a polyalkylene glycol according to the procedure outlined in British Patent Nos. 796,446 and 1,011,118. However, many of these materials have relatively high acidity, causing them to react with and thereby deactiviate certain catalyst systems generally used in the formation of polyurethane polymers such, for example, as tertiary amine compounds. The first method has the additional drawback of contamination of the product by the alkylene glycol by-product, which contamination is not easily removed.

In order to increase the flame retardancy of some of the above described phosphorus compounds, which have low phosphorus content, the prior art has attempted to incorporate various halogen containing substituents into the above described molecules. Thus U.S. Pat. No. 3,159,605 describes the reaction of halogenated methanes with these compounds. Likewise U.S. Pat. Nos. 3,131,206 and 3,328,493 describe the reaction of chloral with them. However, these materials, like their precursors, have many drawbacks. In particular these products have high OH numbers and low phosphorus content thereby rendering them unsuitable as flame retardants in flexible urethane foams.

In the above cited co-pending U.S. applications, there are disclosed novel polyalkylene glycol vinyl phosphates which are far superior as flame retardant for urethane foams, particularly flexible foam, than any of the above described flame retardants. These vinyl phosphates, however, have one drawback. While they yield foams having excellent flame retardants and physical characteristics, they tend to discolor the center of the bun, thereby rendering the foam objectionable in appearance.

It is an object of the present invention to prepare novel polyalkylene glycol polyphosphorus compounds which are suitable as flame retardants for urethane foams, and in particular flexible urethane foams.

It is another object of the present invention to prepare novel polyalkylene glycol polyphosphorus compounds which, while exhibiting flame retardancy and physical properties comparable with those of the flame retardants described in the above cited co-pending applications, yield foams having good color and appearance throughout. Further advantages of the present invention will become obvious from a reading of the disclosure which follows hereinafter.

TECHNICAL DESCRIPTION OF THE DISCLOSURE

It has now been discovered that, by reacting a halogenated carbonyl compound with certain polyalkylene glycol polyphosphites in an amount less than the stoichiometric equivalent, there is obtained a polyalkylene glycol polyphosphorus compound having both phosphite and vinylphosphate linkages along the polymer chain. These polyalkylene glycol polyphosphorus compounds, when incorporated into urethane foams, yield foams having superior flame retardance, physical properties, and little if any discoloration in the bun.

The polyalkylene glycol polyphosphorus compounds of the present invention are polymers containing both phosphite and vinylphosphate linkages. They are characterized by low OH numbers and acidity, a lack of the tendency to gel initially or crosslink in the final foamed product, and high stability during and subsequent to the foam forming process. These compounds can be represented by an idealized formula as follows:

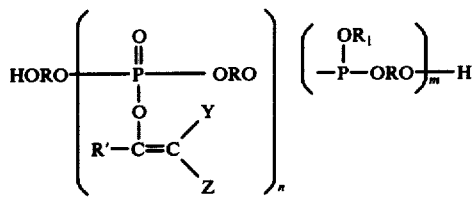

wherein R is a polyalkylene glycol residue; R' either hydrogen, alkyl or haloalkyl; Z and Y are each either hydrogen, halogen, or alkyl; $R_1$ is an alkyl residue from the tertiary phosphite used to produce the polyalkylene glycol alkyl polyphosphite starting material of the present invention; m and n are numbers in the range between from 1 to about 25 such that the sum of m+n is from about 2 to about 50, and preferably between about 4 to about 10. In the above formula, when any of R', X and Z are an alkyl or haloalkyl group, they preferably contain from 1 to about 4 carbon atoms. The term alkyl residue as designated by $R_1$ is preferably $C_{1-10}$ alkyl and most preferably methyl or ethyl. The term halogen and the prefix halo are meant to designate either chlorine or bromine. The term polyalkylene glycol residue, designated by R, is meant to define that portion remaining after two hydroxyl groups have been removed from a polyalkylene glycol having the formula:

wherein R" is an alkylene group of from 2 to about 20 carbon atoms, which is straight chained, branch chained, or a mixture thereof, and x designates the number of repeating alkylene ether units and is normally from 2 to about 20.

The formula for the polyphosphorus compounds shown above, as will be readily appreciated by those skilled in the art, is meant to designate a mixed polymer wherein the phosphite and phosphate linkages are randomly dispersed along the polymer chain. Furthermore, it is understood that the formula encompasses mixtures of polymers having an average chain length of m+n wherein m and n each represent an average value of the number of phosphite and phosphate linkages contained in this mixture rather than just a single pure compound.

The compounds of the present invention are produced by reacting a halogenated carbonyl compound with a polyalkylene glycol alkyl polyphosphite which has an idealized formula as follows:

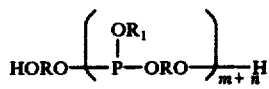

wherein R, $R_1$, m and n are as described as above. This polyphosphite, in turn, is formed by transesterifying a tertiary phosphite with a polyalkylene glycol in a molar ratio of from about 1 to about 1.5 and preferably from 1 to 1.2, moles of phosphite per mole of glycol.

The tertiary phosphite used to prepare the polyalkylene glycol alkyl polyphosphite starting material has the general formula:

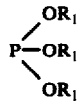

wherein each $R_1$ is as defined above. The phosphites used can be chosen from the following: trimethyl phosphite, triethyl phosphite, tripropyl phosphite, tributyl phosphite, trioctyl phosphite, dimethyl ethyl phosphite, diethyl methyl phosphite, and the like. Trimethyl and triethyl phosphite are particularly preferred, with trimethyl phosphite being most preferred.

The above described tertiary phosphite is transesterified with a polyalkylene glycol having the formula:

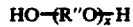

wherein R" and x are as described above. Illustrative of the polyalkylene glycols which can be employed in the present invention are the following: diethylene glycol, triethylene glycol, dipropylene glycol, tripropylene glycol, tributylene glycol, polyethylene glycols wherein the average number of ether units is 2, polypropylene glycols wherein the average number of ether units is 14, trihexylene glycol and the like. Particularly preferred glycols are diethylene glycol, dipropylene glycol and tripropylene glycol. It is understood that these propylene glycols can be primary, secondary or mixtures thereof.

In order to form the polyphosphite starting materials of the present invention, the tertiary phosphite and the polyalkylene glycol must be reacted in critical proportions. Thus, the phosphite should be present in an amount from about 1 to about 1.5 moles per mole of the glycol. The preferred range for this preparation is from about 1 to about 1.2 moles of phosphite per mole of glycol. If the glycol is reacted in quantities greater than 1 to 1 with the phosphite, the product will contain primarily the undesirable mono, di, tri and tetraphosphites and, more importantly, will have a substantial amount of free alkylene hydroxyl groups attached to the phosphite group.

The above disclosed transesterification reaction is normally conducted by mixing the phosphite and glycol in the presence of any of the well known transesterification catalysts. Particularly useful catalysts are the alkali metal alcoholates and phenolates such as sodium methylate, sodium decylate, sodium phenolate, and the like. These catalysts are normally employed in an amount from about 0.01 to about 10 percent, by weight, of the entire reactant mixture. The reaction temperature should initially be kept below the boiling point of the lowest boiling reactant in order to avoid the loss of that reactant. Although the reaction can be conducted at room temperature, i.e. 20° C., it is preferred to conduct it as close to the upper limit as possible in order to increase the rate of reaction. Thus, in the case where trimethyl phosphite is employed as the tertiary phosphite, the reaction temperature is preferably within the range of 80° C. to 100° C. and should not be allowed to rise above 105° C. until at least one $R_1$ group on each of the phosphite molecules has been replaced with a polyalkylene glycol. This can be determined by monitoring the amount of methanol which has been evolved.

While the reaction can be run to completion at these temperature ranges, it has been found to be advantageous to raise the temperature after this initial replacement of one of the $R_1$ group on the starting phosphite Rp to a limit of about 200° C. and most preferably up to about 150° C. As stated above, the point at which the temperature should be raised can be determined by monitoring the amount of by-product alkanol produced. Thus, when one mole of trimethyl phosphite is being transesterified, the reaction temperature can be raised after one mole of methanol has been evolved. The transesterification is completed when two moles of methanol have been evolved. The degree of polymerization of the polyphosphite can be controlled to an extent by varying the time of the reaction. Furthermore, the polymer length can be monitored by measuring the viscosity buildup during the reaction according to well known techniques.

The transesterification reaction can optionally be carried out in the presence of an inert solvent, however, such solvent is not required for the practice of the present invention. The term inert solvent is meant to designate any solvent which does not react with the starting materials or products of the present invention. Suitable solvents include the alkylated benzenes such as ethyl benzene, diethyl benzene, toluene, the xylenes, and the like.

The polyalkylene glycol alkyl polyphosphites produced by the process described above is then reacted with a halogenated carbonyl compound having the formula:

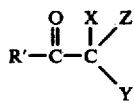

where R', Z and Y are as defined above and X is bromine or chlorine. These carbonyl compounds can be illustrated by the following: chloral, bromal, 1,1,1-trichloroacetone, 1,1;1-tribromoacetone, hexachloroacetone, hexabromoacetone, pentachloroacetone, monochloroacetone, monobromoacetone, dichloroacetaldehyde, dibromoacetaldehyde, chloroacetaldehyde, bromoacetaldehyde, chloromethyl ethyl ketone, dichloromethyl ethyl ketone, trichloromethyl ethyl ketone, bromomethyl ethyl ketone and the like. Preferred carbonyl compounds are chloral, bromal, monochloroacetone, monobromoacetone, trichloroacetone, tribromoacetone, pentachloroacetone, hexachloroacetone, dichloroacetaldehyde and chloromethyl ethy betone. Particularly preferred compounds for use in the present invention are chloral, bromal, monochloroacetone and monobromoacetone.

The carbonyl compound is reacted with the polyphosphite in less than a stoichiometric quantity. The term, "stoichiometric quantity" as used herein, is meant to designate the molar equivalent of phosphite groups in the polyphosphite. By employing less than this quantity, the product will contain unreacted phosphite groups, which stabilize the urethane foam into which it has been incorporated against changes in color. While employing any amount of carbonyl compound less than a stoichiometric quantity will have a color stabilizing effect, the optimum results can be achieved by balancing the flame retardant properties of the vinyl phosphate with the stabilizing properties of the phosphite. The normal range for most foam applications is from about 0.1 to about 0.9 moles of carbonyl compound per mole of phosphite group. The most preferred range for flexible urethane foams is from about 0.6 to about 0.9 moles of carbonyl compound per mole of phosphite group.

The carbonyl compound can be reacted with the polyphosphite over a wide temperature range. Normally temperatures from about 0° to about 150° C. are employed, with the preferred range being from about 20 to about 85° C. The reaction can be monitored by determining the amount of alkyl halide by-product formed. Thus, when 0.6 molar equivalents of carbonyl compound are used, the reaction is completed when 0.6 moles of alkyl halide have evolved.

The reaction with the carbonyl compound is preferably carried out in the presence of a solvent or diluent although this is not necessary to the invention. The solvent helps to control the temperature of the reaction, which is very exothemic in nature, and thereby, eliminates the necessity of cooling the reactants to maintain the proper reaction temperature. The solvent or diluent should be non-reactive with respect to both the starting materials and the desired products, and should be miscible therewith. Illustrative of suitable solvents are benzene, xylene, ethylbenzene, diethylbenzene, various alkanes, and the like.

The novel compounds of the present invention are characterized by their ability to copolymerize with polyisocyanates employed in forming polyurethanes, by their relatively low OH numbers and acidity, by their high phosphorus content, and by their high flame retardancy and stabilizing characteristics in the final foams. These compounds can completely replace the polyols normally employed in forming the foams or they can be used in combination with the polyols, therey yielding foams with greatly improved flame resistance. Since they react in the foam forming process, their residues are chemically bonded into the foam, thereby giving them high permanance, even upon high temperature aging. The acid numbers of the compounds of the present invention are normally below about 2 millegrams of KOH per gram of the polyalkylene glycol polyphosphorus compound. This low acidity makes these compounds relatively unreactive toward the polymerization catalysts employed in producing the polyurethane foams. The vinyl phosphate groups in these compounds reduces the concentration necessary to achieve a flame resistant foam, while the phosphite group stabilizes the foam against discoloration. As mentioned above, these compounds have relatively low OH numbers as compared to the prior art flame retardants and, therefore, can be used in flexible urethane foams without materially affecting the physical properties of such foams. By the term relatively low OH numbers, it is means to designate OH numbers below about 150 and preferably below 100.

The compounds of the present invention are further characterized by the fact that they are substantially linear polymers when compared to those disclosed in the prior art. This results, at least in part, from the fact that the intermediate polyalkylene glycol alkyl polyphosphites used to make the present compounds contain primarily alkyl side chains attached to the phosphite groups. Consequently, the labile halogen released by the attaching carbonyl compound will preferentially react with the alkyl side chain rather than with the glycol linking groups. Thus, it has been observed that the by-product formed by the addition of the carbonyl compound to the polyphosphite intermediate used herein is the alkyl halide rather than the halogenate polyether alcohol which would result from attack on the polyalkylene glycol. Since the phosphite alkyl group is attacked preferentially there is little or no depolymerization.

An additional advantage inherent in the present invention is the fact that the alkyl halide by-product can easily be separated from the desired final product whereas a halogenated polyether alcohol by-product, such as would be formed when using the polymers described in U.S. Pat. No. 3,328,493, cannot be easily separated due to its higher boiling point. Furthermore, the necessity for separating a halogenate polyether alcohol by-product such as would be formed by 3,328,493 is manifest since it is a monofunctional alcohol which would seriously impair, if not destroy, the foam forming ability of the urethane foam mix.

The compounds of the present invention, when employed in sufficient quantity, will yield a self-extinguishing polyurethane foam. This characteristic is particularly important in the area of flexible foams due to the wide use of such foams in hospitals, homes and automobiles. Normally, the compounds of the present invention can be employed in amounts of from about 5 to about 30 percent, by weight, of the entire foam forming mixture to yield self-extinguishing flexible foams. Preferably they are employed in amounts from 10 to 15 percent, by weight, of the entire mixture. It is understood, however, that thin amount will vary depending upon the particular foam being used, and that the required proportions can easily be determined with a minimum amount of blending work.

While the compounds of the present invention are primarily intended for use in urethane foams, it is contemplated that they can also be used in a wide variety of polymeric systems. Illustrative of these systems are: polyesters, polyolefins, cellulose ethers and esters, urethane coatings and elastomers, polymethyl methacrylates, polyvinyl chlorides, and many others. Furthermore, the compounds of the present invention can also be employed in combination with any of the known flame retardants in foams or polymeric systems.

The polyurethane foams within which the flame retardants described above are incorporated are well known in the art. They are produced by the reaction of a di- or polyisocyanate and a di- or polyhydroxy (polyol) compound in the presence of a blowing agent and a catalyst. The foams can be made by any of the basic techniques used in foam formation; i.e., the prepolymer technique, the semi-prepolymer technique or the one-shot process. These techniques are well known and described in the polyurethane art.

As exmples of organic di- and polyisocyanates which can be employed to make the polyurethane foams there can be employed toluene-2,4-disocayanate; toluene-2,6-disocyanate; 4-methoxy-1,3-phenylene diisocyanate; diphenyl methane-4,4'-diisocyanate; 4-chloro-1,3-phenylene-diisocyanate; 4-isopropyl-1,3-phenylene-diisocyanate; 4-ethoxy-1,3-phenylene-diisocyanate; 2,4-diisocyanate-diphenylether; 3,3'-dimethyl-4,4'diisocyanate-odiphenyl methane; mesitylene diisocyanate; durylene diisocyanate; 4,4'-methylene-bis (phenylisocyanate); benzidine diisocyanate; o-nitrobenzidine diisocyanate; 4,4'-diisocyanate-dibenzyl; 3,3'-bitoylene-4,4'-diisocyanate; 1,5-naphthalene diisocyanate; tetramethylene diisocyanate; hexamethylene diisocyanate; decamethylene diisocyanate; toluene-2,4,6-triisocyanate; tritelymethane triisocvanate; 2,4,4'-triisocyanatodiphenyl ether: the reaction product of toluene diisocyanate with trimethylolpropane; and the reaction of toluene diisocyanate with 1,2,6-hexanetriol.

Alternatively, as the polyisocyanate there can be used prepolymers made by reacting one or more of the above polyisocyanates with a di- or polyhydroxy compound such as a polyester having terminal hydroxyl groups, a polyhydric alcohol, glyccrides or hydroxy containing glyccrides, etc. These prepolymers should have terminal isocyanate groups and, to insure their presence, it is frequently desirable to.employ an excess of 5% or more of the polyisocyanate in forming the prepolymer. Typical examples of such prepolymers having isocyanate end groups are those formed from toluene diisocyanate and polyhydroxy compounds. In most cases, a mixture of 8% of the 2,4-isomer and 20% of the 2,6-isomer of toluene diisocyanate is employed in making these prepolymers. Thus, there can be used the prepolymers resulting from the reaction between toluene diisocyanate and caster oil, blown tung oil, blown linseed oil or blown soya oil, and of toluene diisocyanate and the polyester of ethylene glycol, propylene glycol and adipic acid.

Examples of suitable polyols are polyethylene glycol, polypropylene glycols, ethylene glycol, diethylene glycol, triethylene glycol, propylene glycol, dipropylene glycol, tripropylene glycol, 1,4-butanediol, thiodiglycol, glycerol, trimethylolethane, trimethylolpropane, ether triols from glycerine and propylene oxide, other containing triols from 1,2,6-hexanetriol and propylene oxide, sorbitol propylene oxide adducts, pentacrythritol-propylene oxide adducts, trimethylol phenol, oxypropylated sucrose, triethanolamine, pentacrythritol, dicthanolamine, caster oil, blown linseed oil, blown soya oil, N,N,N',N'-tetrakis(2-hydroxyethyl) ethylenediamine, N,N,N',N'-tetrakis(2-hydroxypropyl) ethylenediamine, N,N,N',N'',N''-pentakis(2-hydroxypropyl) diethyl triamine, N,N,N',N'',N''-diethylene pentakis(2-hydroxyethyl) diethylene triamine, mixed ethylene glycol-propylene glycol adipate resin, polyethylene adipate phthalate and polyneopentylene sebacate.

In preparing the foamed polyurethanes there can be used any of the conventional basic catalysts such, for example, as N-methyl morpholine, N-ethyl morpholine, 1,2,4-trimethylpiperazine, trimethyl amine, triethyl amine, tributyl amine and other trialkyl amines, the esterification product of adipic acid and diethylethanolamine, triethyl amine citrate, 3-morpholinopropionamide, 1,4-bis(2-hydroxypropyl)-2-methylpiperazine, 2-diethylaminoacetamide, 3-diethylaminopropionamide, diethylethanolamine, triethylenediamine, N,N,N',N'-tetrakis (2-hydroxypropyl) ethylenediamine, N,N'-dimethylpiperazine, N,N-dimethylhexahydroaniline, tribenzylamine and sodium phenolate. Also, applicable are tin compounds, e.g. hydrocarbon tin acrylates such as dibutyltin dilaurate, dibutyltin diacetate, dibu(y)tin dioctoate, tributyltin monolaurate, dimethyltin diacetate, dioctyltin diacetate, dilauryltin diacetate, dibutyltin maleate, hydrocarbon tin alkoxides, e.g. dibutyltin diethoxide, dibutyltin dimethoxide, diethyltin dibutoxide as well as other tin compounds, e.g. octylstannoic acid, trimethyltin hydroxide, trimethyltin chloride, triphenyltin hydroxide, trimethyltin chloride, triphenyltin hydride, triallyltin chloride, trioctyltin fluoride, dibutyltin dibromide, bis(carboethoxymethyl) tin diiodide, tributyltin chloride, trioctyltin acetate, butyltin trichloride, octyltin tris(thiobutoxide), dimethyltin oxide, dibutyl tin oxide, dioctyltin oxide, diphenyltin oxide, stannous octanoate, and stannous oleate.

Any of the conventional surfactants can be used in amounts of 1% or less, e.g. 0.2% by weight of the composition. The preferred surfactants are silicones, e.g. polydimethyl siloxane having a viscosity of 3 to 100 centistokes, triethoxyoimethyl polysiloxane, molecular weight 850 copolymerized with a dimethoxy polyethylene glycol having a molecular weight of 750.

The foaming reaction can be carried out by adding water to the polyol prior to or simultaneously with the addition of the polyisocyanate. Alternatively, foams can be prepared by the use of a foaming or blowing agent. These are usually a liquefied, halogen substituted alkane such, for example, as methylene chloride. Especially preferred are those halogen substituted alkanes having at least one fluorine atom in their molecules such as trichlorofluoromethane, dichlorodifluoromethane, dichloromonofluoromethane, chlorodifluoromethane, dichlorotetrafluoroethane. In using these blowing agents, they are uniformly distributed in either the polyol reactant or the polyisoctanate reactant whereupon the reactants are mixed permitting the temperature of the mixture to rise during the ensuing reaction above the boiling point of the liquefied gas so as to produce a porous polyurethane. It should be noted that foaming may also be affected by combining the use of a blowing agent with the addition of water to the polyol.

EXAMPLE I

A three-necked flask equipped with a mechanical stirrer, thermometer and distilling head is charged with 268g. (2.0 moles) of dipropylene glycol, 272.8g. (2.2 moles) of trimethyl phosphite and 1.0g. of sodium methoxide. The reactants are then heated slowly to 110° C. A total of 111g. of volatiles are removed and the reaction mixture is then stripped at 103° C with aspirator vacuum. The mixture is subsequently cooled and 200 ml. of benzene is added. The reactant mixture is further cooled by means of an ice bath and 176.4g. (1.2 moles) of chloral is added at a rate sufficient to maintain the pot temperature below about 25° C. The temperature is then raised to 80° C and aspirator vacuum applied. After the volatiles have been removed, 480.4 grams of a viscous liquid product is obtained. The product is neutral and gives the following analysis:

OH number = 28
P% = 10.2 (theoretical 10.3%)
Cl = 20.7 (theoretical 23.6%)

Infrared analysis shows that the product contains both vinylphosphate and phosphite groups.

EXAMPLE 2

The procedure of Example 1 is repeated except that 212g (2.0 moles) of diethylene glycol is substituted for the dipropylene glycol. The resultant product is a viscous oil having a slightly higher P & Cl content than that of Example 1.

EXAMPLE 3

The procedure of Example 1 is again repeated except that 384 grams (2.0 moles) of tripropylene glycol is substituted for the dipropylene glycol. The resultant product has a slightly lower P and Cl content than the product of Example 1.

In like manner to the above examples, bromal, monochloroacetone, monobromoacetone, trichloroacetone, tribromoacetone, pentachloroacetone, pentabromoacetone, hexachloroacetone, hexabromacetone and chloromethyl ethyl ketone give good results when substituted for the chloral in Example 1.

EXAMPLE 4

A 30 gallon reactor fitted with a vacuum distilling column was charged with approximately 26.2 kg. (195 moles) of dipropylene glycol, 26.6 kg. (214 moles) of trimethyl phosphite and 250 grams of a 25% solution of sodium methylate. The pot temperature was raised from 20° C to 80° C over a period of 15 minutes. The temperature was again raised from 80° C to about 102° C over 30 minutes and maintained in the range from 100°-110° C for 45 minutes, during which time a vacuum of 37 mm. was applied. Thereafter about 30 kg. of benzene solvent was added and the temperature was reduced to 54° C. The stepwise addition of 17.4 kg. (118 moles) of chloral was then conducted over a period of 25 minutes while the temperature was allowed to climb to about 69° C. The reactant mixture was allowed to stand for approximately 90 minutes and then vacuum was applied and the temperature was raised to 85° C over a period of 60 minutes. The final yield was 46.5 kg. of yellow oil having the following properties:

$n_D^{23.5}$ = 1.4774
Acid No. = 0.14 mg KOH/g sample
OH No. = 20 mg KOH/g sample
Cl = 23.0%
P = 9.95%

EXAMPLE 5

A polyurethane foam was prepared by employing the following formulation:

| | | |
|---|---|---|
| propylated glycerol (3000 mol. wt.) | 200 | g |
| A polyphosphorus compound prepared according to the procedure of Example 4. | 30 | g |
| silicone surfactant | 1.8 | g |
| Water | 8.0 | |
| N-ethylmorpholine | 0.40 | g |
| 2-(diethylamino)ethyl ether | 0.35 | g |
| 50% stannous octoate in dioctyl phthalate | 0.80 | g |
| toluene diisocyanate (80/20 isomers) | 102.3 | g |

The resultant product was a flexible foam having good color and odor and was self-extinguishing upon dry heat aging at 140° C for 22 hours.

What is claimed is:

1. A flame retardant polyurethane foam containing, as a chemically bonded integral part thereof, the residue of a polyalkylene glycol polyphosphorus compound having the formula:

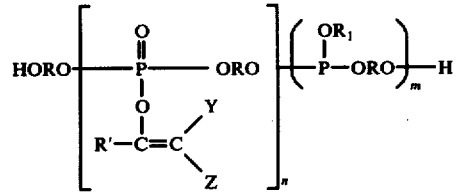

wherein the amount of said compound is from about 5 to 30 percent by weight of said foam and R is a polyalkylene glycol residue defined as that portion remaining after two hydroxyl groups have been removed from a polyalkylene glycol having the formula:

wherein R" is an alkylene group of from 2 to about 20 carbon atoms, which is straight chain, branch chain or a mixture thereof, and $x$ designates the number of repeating alkylene ether units and is from 2 to about 20; $R_1$ is a $C_1$-$C_{10}$ alkyl residue; R' is selected from the group consisting of hydrogen, $C_1$-$C_4$ alkyl, and $C_1$-$C_4$ haloalkyl; Y and Z are each selected from the group consisting of hydrogen, halogen, and $C_1$-$C_4$ alkyl; and $m$ and $n$ are numbers in the range from 1 to about 25 such that the sum of $m$ and $n$ is in the range from about 2 to about 50.

2. The polyurethane foam of claim 1 wherein R is a residue of a polyalkylene glycol selected from the group consisting of triethylene glycol, dipropylene glycol and triproplyene glycol, $R_1$ is methyl, R' is hydrogen and Y and Z are chlorine.

* * * * *